United States Patent [19]

Ackrell

[11] 4,051,149

[45] Sept. 27, 1977

[54] 6,11-DIHYDRODIBENZO-[b.e.]-THIEPIN-11-ONE-3-ACETONITRILE

[75] Inventor: Jack Ackrell, Palo Alto, Calif.

[73] Assignee: Syntex (U.S.A.) Inc., Palo Alto, Calif.

[21] Appl. No.: 697,651

[22] Filed: June 18, 1976

[51] Int. Cl.$^2$ .................................. C07D 337/12
[52] U.S. Cl. ........................................ 260/327 B
[58] Field of Search ............... 260/327 B, 333, 515 R, 260/517

[56] References Cited

U.S. PATENT DOCUMENTS

| | | | |
|---|---|---|---|
| 3,975,437 | 8/1976 | Brunet et al. | 260/558 P |
| 3,979,430 | 9/1976 | Nelson et al. | 260/465 K |

Primary Examiner—Cecilia M. S. Jaisle
Attorney, Agent, or Firm—Gerard A. Blaufarb; William B. Walker

[57] ABSTRACT

6,11-Dihydrodibenzo-[b.e.]-thiepin-11-one-3-acetic acid is prepared from 6,11-dihydrodibenzo-[b.e.]-thiepin-11-one-3-acetonitrile, a novel intermediate, by strong acid or base hydrolysis.

1 Claim, No Drawings

6,11-DIHYDRODIBENZO-[b.e.]-THIEPIN-11-ONE-3-ACETONITRILE

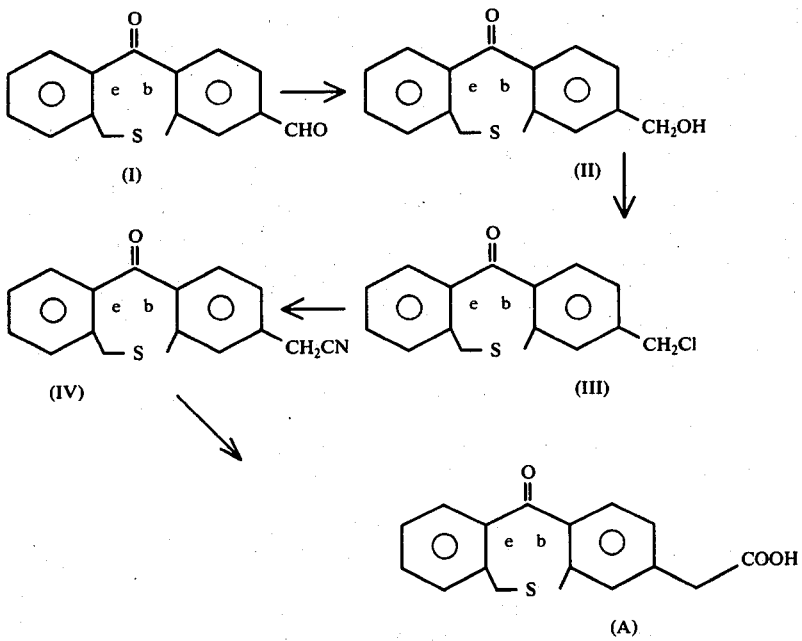

The present invention relates to a novel process for the preparation of 6,11-dihydrodibenzo-[b.e.]-thiepin-11-one-3-acetic acid, represented by the formula:

(A)

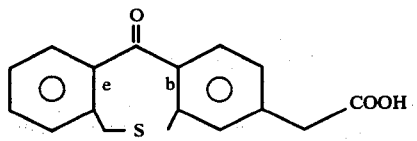

by acid or base hydrolysis of 6,11-dihydrodibenzo-[b.e.] thiepin-11-one-3-acetonitrile, a novel intermediate.

The compound of Formula (A) and the esters and pharmaceutically acceptable salts thereof are useful as anti-inflammatory, antipyretic and analgesic agents, platelet aggregation inhibitors, fibrinolytic agents, and as smooth muscle relaxants. They can be used both prophylactically and therapeutically.

Thus, the compositions containing these compounds are useful in the treatment and elimination of inflammation such as inflammatory conditions of the muscular skeletal system, skeletal joints and other tissues, for example, in the treatment of inflammatory conditions such as rheumatism, concussion, laceration, arthritis, bone fractures, post-traumatic conditions, and gout. In those cases in which the above conditions include pain and pyrexia coupled with inflammation, the instant compounds are useful for the relief of these conditions as well as the inflammation.

The compound of Formula (A) and the esters and pharmaceutically acceptable salts thereof are also uterine smooth muscle relaxants and thus are useful as agents for maintaining the pregnancy of pregnant mammals, for the benefit of the mother and/or the fetus, until termination of the pregnancy is considered, from a medical point of view, to be favorable, or more favorable, for the mother and/or the fetus.

The novel process of the present invention can be illustrated by the following reaction sequence:

In practicing the process outlined above, the starting material of Formula (I), i.e., 6,11-dihydrodibenzo-[b.e.]-thiepin-11-one-3-aldehyde, disclosed in copending U.S. application Ser. No. 697,648, filed on even date herewith, is selectively reduced at the 3-position, to afford 3-hydroxymethyl-6,11-dihydrodibenzo-[b.e.]-thiepin-11-one, the compound of Formula (II). This selective reduction is effected by using sodium triacetoxyaluminum hydride as reagent (prepared from sodium borohydride and glacial acetic acid) in an aprotic solvent, e.g., benzene, xylene, dimethoxy ethane, N-methyl pyrrolidone and the like, at about 0° C to about 100° C, preferably at room temperature, for about 6 to about 24 hours, under an inert atmosphere, e.g., under nitrogen atmosphere.

Upon reaction of 3-hydroxymethyl-6,11-dihydrodibenzo-[b.e.]-thiepin-11-one with thionyl chloride, optionally in the presence of an inert solvent such as methylene chloride, toluene, diethyl ether and the like, at a temperature of from about 0° C to about 100° C, preferably at room temperature, for about 30 minutes to about 4 hours, there is obtained 3-chloromethyl-6,11-dihydrodibenzo-[b.e.]-thiepin-11-one, the compound of Formula (III), which is converted into 6,11-dihydrodibenzo-[b.e.]-thiepin-11-one-3-acetonitrile, the compound of Formula (IV), a novel intermediate, by treatment with sodium cyanide in the presence of a buffer, e.g., using aqueous magnesium sulfate as buffer. The reaction is conducted in an inert, water miscible organic solvent such as dimethylformamide, dimethylacetamide, dimethylsulfoxide, N-methyl pyrrolidone and the like, under an inert atmosphere, at about 0° C to about 50° C, preferably at room temperature for about 6 to about 24 hours.

The novel nitrile compound (IV) is converted into the desired 6,11-dihydrodibenzo-[b.e.]-thiepin-11-one-3-acetic acid, the compound of Formula (A) by acid or base catalyzed hydrolysis.

Acid catalyzed hydrolysis is effected by reaction with a strong acid such as a mineral acid, e.g., phosphoric acid, sulfuric acid, hydrochloric acid and the like, in mixture with acetic acid, at a temperature of from about 60° C to the reflux temperature of the reaction mixture, for about 45 minutes to about 6 hours, the reaction time depending upon the temperature at which the reaction takes place.

In the preferred embodiments, the reaction is effected using a 1:1 mixture of phosphoric acid:acetic acid, at reflux temperature for about 1 hour.

Base catalyzed hydrolysis is accomplished by using a strong base, i.e., an alkali metal hydroxide such as sodium hydroxide, potassium hydroxide or lithium hydroxide in an aqueous high boiling inert organic solvent, e.g., ethylene glycol and propylene glycol, at a temperature of from about 120° to about 220° C, preferably at reflux, for a period of time ranging from about 30 minutes to about 5 hours. The reaction affords initially the salt corresponding to the base used, which may be readily converted into the free acid by treatment with a strong acid for example, a strong mineral acid, e.g., hydrochloric acid, sulfuric acid, phosphoric acid and the like.

It is to be understood that isolation of the compounds described herein can be effected, if desired, by any suitable separation or purification procedure, such as, for example, extraction, filtration, evaporation, distillation, crystallization, thin-layer chromatography or column chromatography, or a combination of these procedures. Illustrations of suitable separation and isolation procedures can be had by reference to the Preparation and Examples herein below. However, other equivalent separation or isolation procedures could, of course, also be used.

By the term room temperature is meant a temperature of from about 18° to about 25° C.

A further understanding of the invention can be had from the following non-limiting Preparation and Examples.

PREPARATION

A. To 20 ml. of benzene there are added, under a nitrogen atmosphere, 1.2 g. of sodium borohydride and 6 ml. of acetic acid, and the resultant mixture is refluxed for 15 minutes. It is then cooled to room temperature and 1 g. of 6,11-dihydrodibenzo-[b.e.]-thiepin-11-one-3-aldehyde (I) is added. The reaction mixture is stirred at room temperature for 16 hours, under a nitrogen atmosphere, poured into water and extracted with ethyl acetate. The combined extracts are washed with water to neutrality, dried over sodium sulfate and evaporated to dryness under reduced pressure, to yield 1 g. of crude 2-hydroxymethyl-6,11-dihydrodibenzo-[b.e.]-thiepin-11-one (II), m.p. 103°-104° C.

A solution of 1 g. of the foregoing crude hydroxymethyl compound in 2 ml. of thionyl chloride is stirred at room temperature for 2.5 hours and then evaporated to dryness under reduced pressure. The residue is dissolved in methylene chloride and filtered through a column of Florisil (20 g.), using methylene chloride:hexane (1:9) as eluant, to produce 1 g. of 3-chloromethyl-6,11-dihydrodibenzo-[b.e.]-thiepin-11-one (III), m.p. 118°-119° C.

EXAMPLE 1

To a solution of 500 mg. of 3-chloromethyl-6,11-dihydrodibenzo-[b.e.]-thiepin-11-one in 20 ml. of dimethylformamide is added, under a nitrogen atmosphere, a solution of 20 mg. of magnesium sulfate in 2 ml. of water followed by 200 mg. of sodium cyanide. The reaction mixture is stirred for 16 hours at room temperature, poured into 200 ml. of iced sodium chloride solution and the formed precipitate collected by filtration. This material is crystallized from methylene chloride-methanol, the crystalline product discarded and the mother liquors evaporated to dryness under reduced pressure, to afford 300 mg. of crude 6,11-dihydrodibenzo-[b.e.]-thiepin-11-one-3-acetonitrile, (IV), m.p. 104°-106° C.

EXAMPLE 2

A solution of 100 mg. of 6,11-dihydrodibenzo-[b.e.]-thiepin-11-one-3-acetonitrile (IV) in 2 ml. of a 1:1 mixture of acetic acid: phosphoric acid is refluxed for one hour, cooled and poured into water. The product is extracted with ethyl acetate (3 × 10 ml.), and the combined extracts are washed with 10% sodium carbonate solution. The alkaline phase is acidified with dilute hydrochloric acid and extracted several times with ethyl acetate. The combined extracts are dried over sodium sulfate and evaporated to dryness, to yield 50 mg. of 6,11-dihydrodibenzo-[b.e.]-thiepin-11-one-3-acetic acid (A), m.p. 152°-153° C, identical to an authentic sample.

Similar results are obtained substituting sulphuric acid or hydrochloric acid for phosphoric acid in the above procedure.

EXAMPLE 3

To a mixture of 3 ml. of ethylene glycol, 2 ml. of water and 50 mg. of potassium hydroxide there are added 100 mg. of 6,11-dihydrodibenzo-[b.e.]-thiepin-11-one-3-acetonitrile (IV), and the resulting mixture is stirred and reluxed for 3 hours under an atmosphere of nitrogen. It is then cooled, 10 ml. of water are added and the mixture is filtered through Celite (diatomaceous earth). The filtrate is acidified with dilute hydrochloric acid and the formed precipitate collected by filtration, thus obtaining 30 mg. of 6,11-dihydrodibenzo-[b.e.]-thiepin-11one-3-acetic acid, m.p. 152°-153° C, identical to an authentic sample.

In a similar manner, other strong bases, e.g., sodium hydroxide and other strong acids, e.g., sulphuric acid and phosphoric acid can be substituted in the above procedure.

What is claimed is:
1. 6,11-Dihydrodibenzo-[b.e.]-thiepin-11-one-3-acetonitrile.

* * * * *